United States Patent [19]
Reynolds

[11] Patent Number: 5,401,253
[45] Date of Patent: Mar. 28, 1995

[54] INTRAVENOUS INFUSION OF PHARMACEUTICALS

[76] Inventor: David L. Reynolds, P.O. Box 600, 305 Knowlton Road (Knowlton), Lac Brome, Quebec, Canada, J0E 1V0

[21] Appl. No.: 180,483

[22] Filed: Jan. 12, 1994

[30] Foreign Application Priority Data

Jan. 12, 1993 [GB] United Kingdom ............... 9300481

[51] Int. Cl.$^6$ ..................... A61M 5/24; A61M 5/28
[52] U.S. Cl. .................... 604/206; 604/201; 604/218
[58] Field of Search ............. 604/154, 155, 283, 188, 604/190, 201, 205, 206, 218, 905, 239, 240, 241, 242, 243, 403, 406

[56] References Cited

U.S. PATENT DOCUMENTS

| | | | |
|---|---|---|---|
| 3,884,229 | 5/1975 | Raines | 604/205 |
| 3,916,894 | 11/1975 | Cloyd | 604/206 |
| 4,084,588 | 4/1978 | Koenig | 604/205 |
| 4,576,594 | 3/1986 | Greenland | |
| 4,623,343 | 11/1986 | Thompson | 604/405 |
| 4,787,898 | 11/1988 | Raines | |
| 4,834,744 | 5/1989 | Ritson | |
| 4,857,068 | 8/1989 | Kahn | |
| 5,114,033 | 5/1992 | Golias | 604/201 |
| 5,137,511 | 8/1992 | Reynolds | 604/88 |

FOREIGN PATENT DOCUMENTS

0378141 8/1990 European Pat. Off.

Primary Examiner—John G. Weiss
Attorney, Agent, or Firm—Ridout & Maybee

[57] ABSTRACT

A system for the intravenous infusion of pharmaceuticals uses a syringe assembly, and a flexible tube for connection to a Y-connector in an intravenous drip assembly through which tube diluent fluid may flow from the drip assembly through the connector assembly to the syringe body, and through which diluted, dissolved or suspended pharmaceutical may pass from the syringe body to the Y-connector. The syringe assembly has an elongated body, a piston movable longitudinally within and in sealing engagement with the body, a plunger for insertion into one end of the body to move the piston, a penetrable closure at the other end of the body, and a connector assembly for establishing a passage for liquid between the interior of the body and the tube, the connector assembly comprising first and second cannulas projectable through said penetrable closure, a coupling for establishing connection between the first cannula and the tube, an air valve establishing a controlled connection to the exterior of the connector assembly, and a connection between the second cannula and the air valve.

7 Claims, 4 Drawing Sheets

INTRAVENOUS INFUSION OF PHARMACEUTICALS

This invention relates to the intravenous (IV) infusion of pharmaceuticals, and to a syringe assembly for use in such infusion.

Various systems have been developed for such infusion. Typically a Y-connector is provided in a tube connecting a bag providing a primary supply of IV fluid, proximate to the site of entry to the patients vein, and a source of the pharmaceutical dissolved or suspended in a suitable diluent, is connected to the Y-connector. The source may be a smaller secondary flexible bag or minibag into which is introduced a suitable dosage of the pharmaceutical, or a syringe operated by a syringe pump such as those sold under the trademark BARD. The minibags have the disadvantage that they must be exchanged at intervals to provide a required dosage regimen over an extended period, and must be prepared as required if the pharmaceutical is one which is not stable in dissolved or suspended form. The more sophisticated models of syringe pump are capable of providing a required programmed dosage regimen over an extended period, but the syringe providing a source of the pharmaceutical must still be prepared before introduction of the system where the pharmaceutical is one which is unstable after dilution, dissolution or suspension, or for some other reason cannot be distributed in ready-to-administer form.

In my U.S. Pat. No. 5,137,511, I describe a syringe system which has particularly utility for the distribution in prefilled syringes of pharmaceuticals which present the problems outlined above, and such a system is particularly well suited for employment in the present invention although certain other syringe systems in which a syringe containing one component of a pharmaceutical preparation requires dilution, dissolution or suspension in a second liquid component could possibly be utilized within the scope of the appended claims. I have devised a modified syringe system and a way to utilize such a syringe system to provide an improved means to administer, by intravenuous infusion, pharmaceuticals which require the addition of a liquid diluent, solvent or carrier shortly prior to administration.

The invention is as set forth in the appended claims.

The invention is described further with reference to the accompanying drawings, in which.

Figure 1:
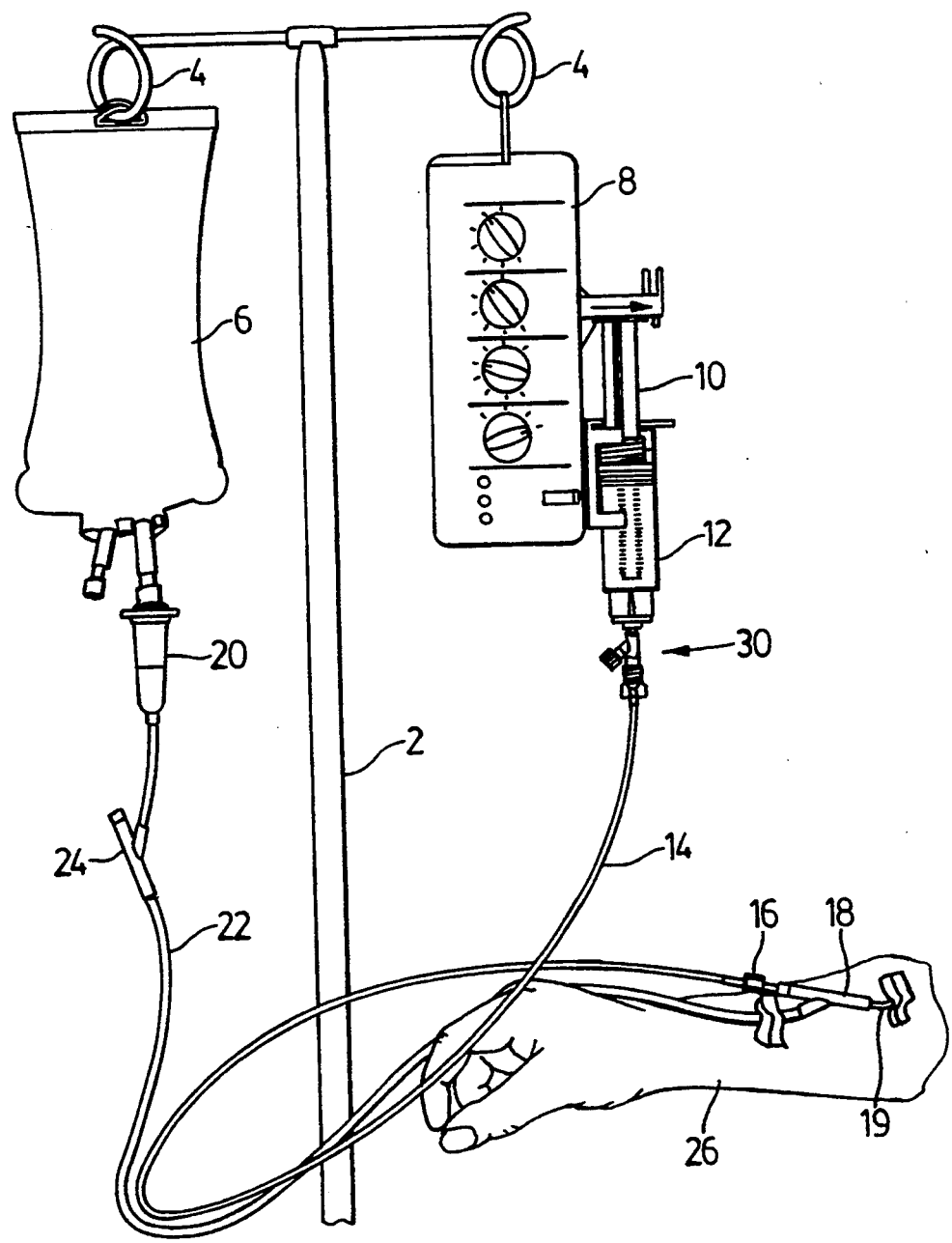
FIG. 1 is a general view of a system for intravenous infusion of a pharmaceutical incorporating the invention.

Referring first to FIG. 1, a conventional IV stand 2 (of which only an upper part is shown) has hooks 4 which support respectively a conventional IV bag 6 and a programmed syringe pump 8, such as that sold by Bard Medsystems under the trademarks BARD and HARVARD MINI-INFUSER. The syringe pump progressively drives the plunger 10 of a syringe whose body 12 is held in the pump so as to deliver the contents of the syringe in a programmed manner through a tube 14 and a connection 16 to a Y-connector 18 where it blends with IV fluid flowing from the bag 6, through a drip-feed 20 and a tube 22 which may contain a further Y-connector 24, before entering a patient 26 through a cannula (not shown), all in a manner well known in the art.

The syringe is connected to the tube 14 by a special connector assembly 30 described further below, whilst the syringe itself is similar to that disclosed in International Patent Application WO92/08507. The syringe is based on a "bottomless vial" which can be filled with a solid or liquid pharmaceutical preparation 40 using a conventional vial filling line, which preparation if liquid may if desired be subsequently lyophilised, in situ in the vial. A piston 32 which closes the open bottom of the vial may be secured against expulsion during terminal sterilization of the contents of the vial by a retainer 34 which is pressed into place after filling and capping of the vial, and is retained by an internal bead 36.

Figure 4C:
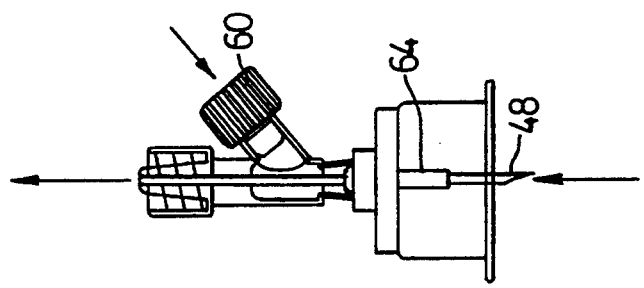
FIGS. 4A, 4B and 4C are views of a connector assembly associated with a syringe shown in the previous figures, illustrating different stages in preparation of the syringe.
Figure 4B:
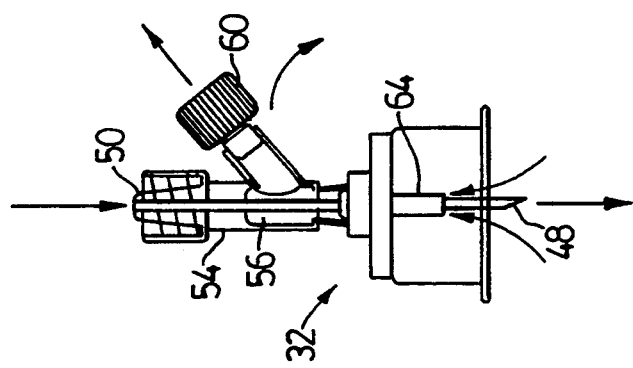
Figure 4A:
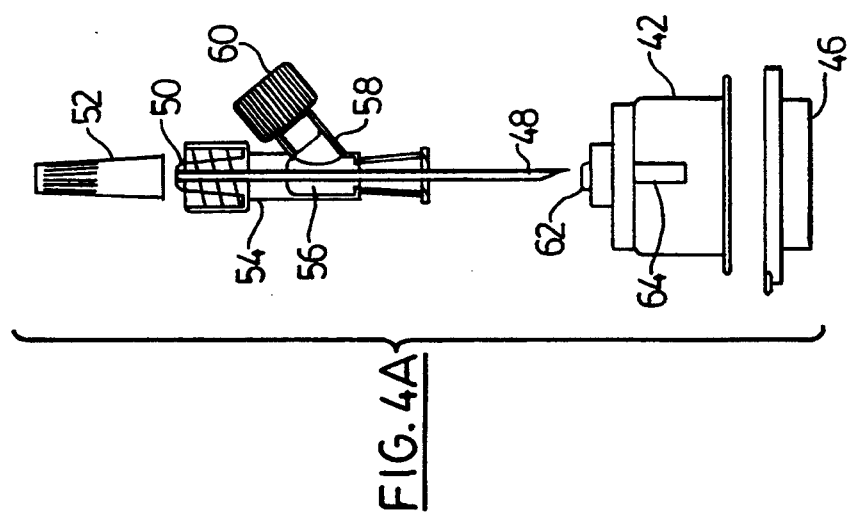

In order to complete the syringe and prepare it for use in the present invention, the connector assembly 30 shown exploded in FIG. 4A is applied. The connector assembly 30 comprises an outer cap 42, which can be press fitted onto an inner annular vial cap 44 which retains an elastomeric closure in the neck of the vial, the vial cap and closure being applied as part of the filling and capping of the vial. Prior to use, the bottom of the cap 42 is sealed against contamination by a removable closure 46 of sufficient depth to accommodate a lower end of a first cannula member in the form of a hollow needle 48, an opposite end of which is secured within a standard male connector 50 formed at the top of a body 54 of the connector assembly and protected prior to use by a removable cap 52.

The body 54 defines a passage 56 which concentrically surrounds the needle 48, and is formed with a side arm 58 equipped with a screw-on air valve 60 which may be unscrewed to allow air to pass in and out of the passage 56, and may incorporate an internal filter (not shown) to ensure against contamination being drawn into the assembly through the valve. A standard female connector at the bottom of the body 54 attaches it to a male connector 62 on top of the cap 42, so that the needle 48 passes concentrically through a second cannula member 64 formed integrally with the cap 42.

Figure 2:
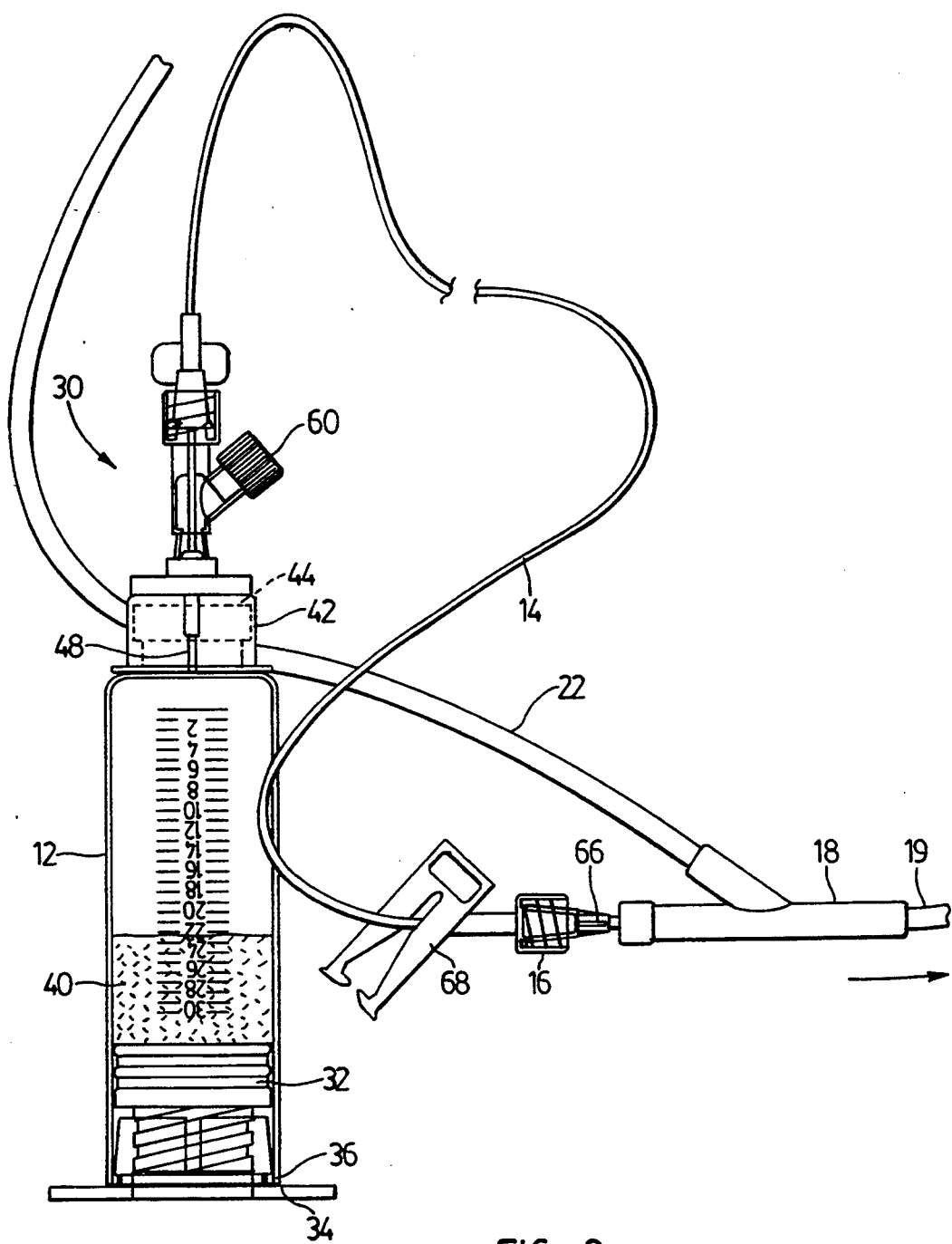
FIGS. 2 and 3 are enlarged views of a syringe assembly and associated parts of the system at different stages during use.

In preparing the system for use (see FIG. 2), the tube 14 is connected to the Y-connector 18 through the connection 16 by means of a needle 66 secured to a male coupling on one end of the tube 14 and inserted through a seal in an end of the Y-connector. The tube 14 is closed by a clamp 68, and a female coupling at its opposite end is attached to the coupling 50.

The cap 42 of the connector assembly 30, after removal of the closure 46, is pressed down over the vial cap 44 so that both the needle 48 and the cannula member 64 penetrate the elastomeric closure of the vial, thus establishing flow connection both between the vial and the tube 14 through the needle and between the vial and the passage 56 through the cannula member 64.

Figure 3:
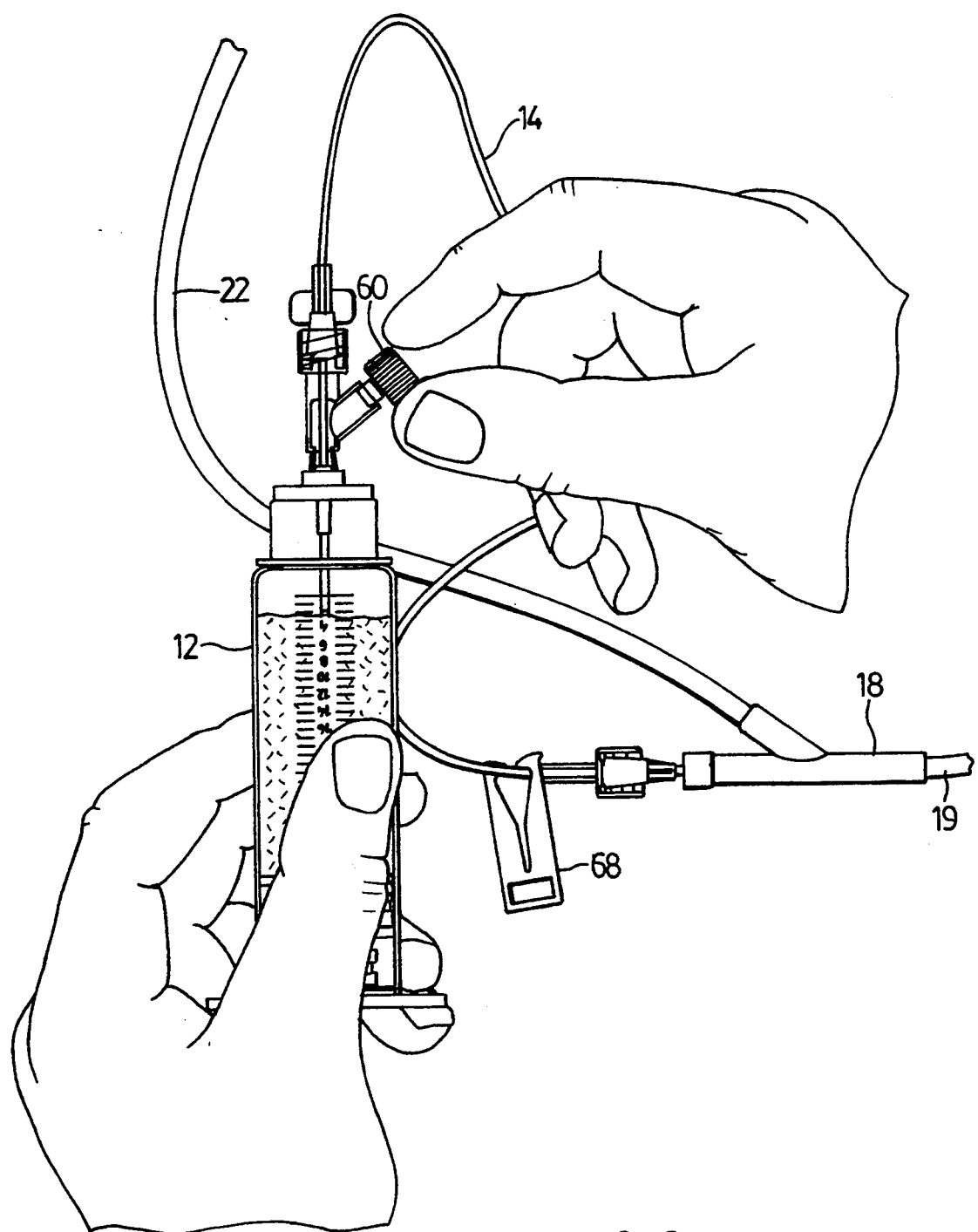

The valve 60 is then opened and the clamp 68 released as in FIGS. 3 and 4B so that fluid from the IV bag can flow via the tube 22, the Y-connector 18, the connection 16, the tube 14 and the needle 48 into the syringe body 12 where it mixes with and dissolves, dilutes or suspends the preparation 40. It should be understood that the syringe will be held during this process at a level lower than the bag 6 and the drip-feed 20 so that hydrostatic pressure will cause the desired liquid flow. It will also be understood that the preparation 40 must be such that the content of the bag will be a suitable diluent, solvent or carrier. It may be desirable temporarily to apply a clamp to a tube portion 19 downstream of the Y-connector 18 so that fluid flow from the bag 6 may be increased without adversely affecting the patient.

As the fluid enters the vial, the air that it displaces escapes through the passage 56 and the valve 60. The valve 60 is closed when a desired amount of fluid has been admitted, as shown by a scale of the syringe body, and the vial may be shaken to assist dissolution or suspension of the preparation 40. The clamp 68 is reapplied once an appropriate amount of liquid has been admitted. The plunger 10 is connected to the piston 32, and the valve 60 may again be loosened to allow residual air to be expelled, after which it is finally closed and the syringe mounted to the pump 8 as shown in FIG. 1. The clamp 68 is again removed and the pump activated so that pressure on the piston 32 causes the contents of the syringe to be expelled in a manner controlled by the programming of the pump 8, through the needle 48 and the tube 14 into the Y-connector 18, whence it is infused into the patient together with fluid from the bag 6.

In some instances, the syringe pump 8 may be dispensed with, where programmed dosage and/or precisely controlled rate of administration are not important, by suspending the syringe from a hook 4 by means of a hook on the plunger, and slightly loosening the valve 60 to allow air to enter the syringe as its contents are drawn out by gravity through the needle 48.

Although a manually operated valve 60 is described, an automatic valve could be employed. A ball valve operated by a combination of gravity (opening when the syringe is pointing upward and closing when it is pointing downward, operating in response to negative pressure within the syringe and closing in response to positive pressure within the syringe) is one possibility. A valve which permits passage of air but not liquid is another possibility. Such valves are known in the art and may be employed provided that reliable operation without admission of contamination can be achieved.

The system described enables prepackaged dosages of pharmaceutical preparations to be manufactured utilizing a conventional vial filling and capping line, to be reconstituted at bedside as required, and, with the aid of a syringe pump, to be administered in a programmed manner over an extended period. Moreover, the use of fluid passing through the tube 14 to prepare the pharmaceutical contained in the syringe means that this tube is filled with liquid prior to the commencement of operation of the pump, thus avoiding the need for a separate priming operation.

I claim:

1. A system for the intravenous infusion of pharmaceuticals, comprising:

a syringe assembly prefilled with a pharmaceutical preparation requiring dilution, dissolution or suspension in a liquid medium prior to administration, the assembly comprising an elongated body, a piston movable longitudinally within and in sealing engagement with the body, a plunger for insertion into one end of the body to move the piston, a penetrable closure at the other end of the body, and a connector assembly for establishing a passage for liquid between the interior of the body and a liquid conduit, the connector assembly comprising first and second cannula means projectable through said penetrable closure, means for establishing connection between the first cannula means and the liquid conduit, an air valve establishing a controlled connection to the exterior of the connector assembly, and means establishing connection between the second cannula means and the air valve; and a flexible tube for connection to a Y-connector in an intravenous drip assembly through which diluent fluid may flow from the drip assembly through the connector assembly to the syringe body, and through which diluted, dissolved or suspended pharmaceutical may pass from the syringe body to the Y-connector.

2. A system according to claim 1, wherein the cannula means are concentric.

3. A system according to claim 2, wherein the first cannula means is a hollow needle passing through the second cannula means and supported by the means for establishing connection to the fluid conduit.

4. A system according to claim 3, wherein the second cannula means is integral with a cap which is pressed over said other end of the syringe body to project said first and second cannula means through said penetrable closure.

5. A system according to claim 1, wherein the syringe body is a bottomless pharmaceutical vial in which the penetrable closure is an elastomeric closure secured in a neck at the top of the vial.

6. A system according to claim 1 in which the plunger is initially detached from the piston.

7. A system according to claim 1, wherein the air valve is manually operated.

* * * * *